United States Patent [19]

Stein

[11] 4,301,285

[45] Nov. 17, 1981

[54] SYDNONIMINE CNS STIMULANTS

[75] Inventor: Reinhardt P. Stein, Audubon, Pa.

[73] Assignee: American Home Products Corporation, New York, N.Y.

[21] Appl. No.: 193,041

[22] Filed: Oct. 2, 1980

[51] Int. Cl.$^3$ .................. C07D 413/12; C07D 271/04
[52] U.S. Cl. ..................................... 544/138; 544/238; 544/333; 544/335; 544/367; 546/187; 546/209; 548/125; 260/244.4; 260/245.5
[58] Field of Search ............... 544/138, 238, 333, 335, 544/367; 546/187, 209; 548/125; 260/244.4, 245.5

[56] References Cited

U.S. PATENT DOCUMENTS 3,277,108 10/1966 Daeniker ............................ 548/125

FOREIGN PATENT DOCUMENTS 2028880 12/1971 Fed. Rep. of Germany .
2738022  6/1978 Fed. Rep. of Germany .
 329890 11/1972 U.S.S.R. .
 222370  5/1973 U.S.S.R. .

OTHER PUBLICATIONS

Olovyanishinkiva et al., *Khim. Geter. Soedin*, vol. 2, (1978), pp. 170-175 and vol. 9, (1975), pp. 1198-1203.
Yashunskii et al., *J. Med. Chem.*, vol. 14, (1971), pp. 1013-1015.
Polgar et al., *Acta. Pharm. Hung.*, vol. 48, suppl., 23-24, (1978).
Polgar et al., *Xenobiotica*, vol. 9, (1979), pp. 511-520.
Kholodov et al., *Mater. Resp. Rasshir, Konf. Farmecol. Gruz.*, 2nd 1977, pp. 84-85.

*Primary Examiner*—Henry R. Jiles
*Assistant Examiner*—R. W. Ramsuer
*Attorney, Agent, or Firm*—Richard K. Jackson

[57] ABSTRACT

This application provides a novel process for the synthesis of 3-[1(hydroxymethyl)-2-phenylethyl]-N-[(phenylamino)carbonyl]sydnonimine derivatives and novel hydrophobic and hydrophilic acyl derivatives thereof as pro-drug central nervous system stimulants.

9 Claims, No Drawings

SYDNONIMINE CNS STIMULANTS

BACKGROUND OF THE INVENTION

After the discovery of the central nervous system stimulatory properties of 3-(1-methyl-2-phenylethyl)-N-(phenylcarbamoyl)sydnone imine (Sydnocarb; U.S.S.R. No. 329,890 and Offenlegungsschrift 2,028,880) various analogues have been reported. U.S.S.R. No. 222,370 and Offenlegungsschrift No. 2,738,022 disclose sydnone imines which contain phenyl, 1- or 2-phenylethyl and the phenylisopropyl groups in 3-position as well as N-meta- and para-chlorophenyl and N-phenyl carbamoyl groups. Variations of 3-benzyl sydnonimines are disclosed in U.S. Pat. No. 3,277,108. Other variously substituted 3-aralkyl sydnonimines are disclosed by Olovyanishinkiva et al., Khim. Geterotsikl Soedin, 2, 170–175 (1978) and 9, 1198–1203 (1975).

Sydnocarb is conventionally produced by cyanomethylation of amphetamine followed by nitrosation and ring closure with a mineral acid to yield sydnophen as an acid halide salt which is reacted with phenylisocyanate under mildly basic conditions to introduce the N-phenylcarbamoyl group. As an asymmetric compound, amphetamine may be employed as the initial reactant as the racemic d,l-mixture or as the pure d- or l-isomer to yield racemic or optically active sydnophen and ultimately sydnocarb.

Yashunskii et al., J. Med. Chem., 14, 1013–1015 (1971) disclose the marked CNS-stimulatory effect of 3-(1-methyl-2-phenylethyl) sydnonimine (Sydnophen). The relative activities of a large number of alkyl, aryl and aralkylsydnonimines are presented in Table 1 on page 1014. Most of them including compound XVIII (2-hydroxy-1-methyl-2-phenylethyl-sydnonimine), were essentially inactive central nervous system stimulants relative to compound XIII (Sydnophen), demonstrating the criticality of the structure of the 3-substituent in the Sydnocarb series of compounds as far as CNS stimulatory activity is concerned. Thus, although the activity profile of Sydnocarb is not identical to that of amphetamine, or for that matter Sydnophen, CNS stimulatory activity is a common property of the initial reactant amphetamine, the intermediate Sydnophen and the final product Sydnocarb.

Although Sydnocarb and its derivatives disclosed in the literature form salts with various organic and inorganic acids, such salts are not appreciably water soluble and when stirred in water, the complex or adduct salt is broken up to reisolate the neutral mesoionic sydnone imine substrate. The salts of sydnocarb are not true salts, in the classical sense, in that they do not dissociate in water to form water soluble ions consisting of the protonated substrate and the corresponding anion derived from the acidifying agent.

The metabolites of Sydnocarb have been studied by several groups. L. E. Kholodov and E. T. Lilin, Mater. Resp. Rasshir. Konf. Farmacol. Gruz 2nd 1977, 84–5 report finding hydroxylation of Sydnocarb at the beta carbon of the phenylisopropyl substituent and at the phenyl ring of the phenylcarbamoyl group, hydrolytic cleavage of the phenylcarbamoyl group and ring opening of the heterocyclic nucleus. They report that the psychostimulating activity of Sydnocarb is a property of that compound and not its metabolites. Polgar et al., Acta. Pharm. Hung., 48, Suppl. 23–24 (1978) and Xenobiotica, 9, No. 8, 511–520 (1979) report several hydroxylated metabolites and conjugates of hydroxylated metabolites.

The compounds of my copending application Ser. No. 194,702 filed concurrently herewith, were prepared by conventional techniques analogous to those employed in the preparation of Sydnocarb. Thus, a properly substituted phenylethanolamine is cyanomethylated with a reactant $XCH_2CN$ where X may be —OH, —Br, —Cl, tosyl, and the like to form the intermediate:

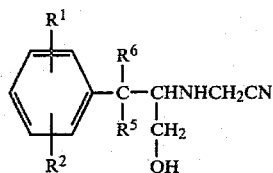

which is nitrosated with an excess of $NaNO_2$ in aqueous HCL to yield the nitroso-nitrile:

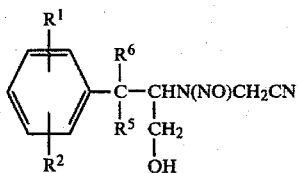

which upon treatment with HCl (anhydrous or in an alkanol, preferably isopropanol) yields the sydnonimine salt:

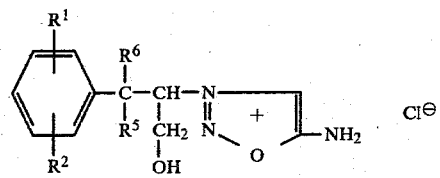

which when reacted as an alcoholic suspension (methanol, ethanol, isopropanol, etc.) with

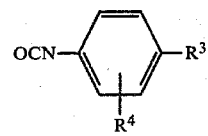

in the presence of a mild base such as sodium acetate yields the desired 3-[1-(hydroxymethyl)-2-phenylethyl]-N-[(phenylamino)carbonyl]-sydnonimine derivatives.

BRIEF DESCRIPTION OF THE INVENTION

This invention provides (1) an improved process for the production of 3-[1-(hydroxymethyl)-2-phenylethyl]-N-[(phenylamino)carbonyl]-sydnonimine derivatives disclosed in copending U.S. Patent Application Ser. No. 194,702, filed concurrently herewith, (2) intermediate compounds produced in that improved process which are in themselves central nervous system stimulants comparable in potency to the final products of said copending application and which afford pro-drugs with hydrophobic or hydrophilic characteristics, and (3) a group of pro-drug compounds which are preparable directly by the process of this invention or from the products of said copending application, Ser. No. 194,702.

DETAILED DESCRIPTION OF THE INVENTION

This invention provides a process for the production of a group of central nervous system stimulants which are 3-[1-(hydroxymethyl)-2-phenylethyl]-N-[(phenylamino)carbonyl]sydnonimines optionally substituted in either or both phenyl rings of the formula:

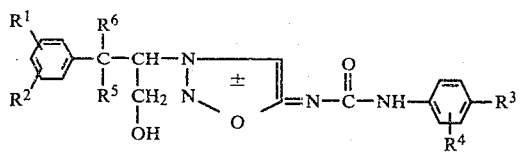

in which $R^1$ and $R^2$ are, independently, hydrogen, alkyl of 1 to 6 carbon atoms, alkoxy of 1 to 6 carbon atoms, halo, perfluoroalkyl of 1 to 3 carbon atoms, nitro, alkanoyl of 2 to 4 carbon atoms, or alkoxycarbonyl of 2 to 4 carbon atoms;

$R^3$ is hydrogen, halo, nitro or alkanoyl of 2 to 4 carbon atoms;

$R^4$ is hydrogen, halo, nitro or perfluoroalkyl of 1 to 3 carbon atoms;

$R^5$ and $R^6$ are, independently, hydrogen, methyl or ethyl;

or a non-toxic acid addition salt thereof.

It is generally preferred that the halo substituent be chlorine, bromine or fluorine although iodine is acceptable. Likewise, it is preferred that the alkyl and alkoxy substituents be relatively small, the methyl, ethyl, propyl, isopropyl, methoxy, ethoxy, propoxy and isopropoxy groups being preferred. The $R^3$ substituent in 4 position when $R^4$ is hydrogen influences potency to a greater extent than $R^1$, $R^2$ and $R^4$ and is preferably a halogen. The non-toxic acid addition salts of the compounds are conventionally produced by the method and from any of the acids disclosed in U.S. Pat. No. 3,277,108. The adduct products are preferably formed with hydrochloric, hydrobromic, sulfuric, phosphoric, phosphorous, acetic, propionic, fumeric, oxalic, succinic or maleic acid.

The 3-[1-(hydroxymethyl)-2-phenylethyl]sydnonimine compounds produced by the process of this invention contain one chiral center bearing the —CH$_2$OH group and optionally another at the benzylic carbon atom, depending upon the character of $R^5$ and $R^6$. When $R^5$ and $R^6$ are hydrogen, activity resides primarily in the l-isomer although mixtures of the d and l isomers are active stimulants and the mixtures need not be separated for practical use applications.

It has now been discovered that the hydroxymethyl substituted nitroso-nitrile intermediates disclosed in my said copending application can be directly converted to the desired Sydnocarb derivatives without separate production of the Sydnophen intermediate. Thus, the step of cyclization of the nitroso-nitrile to obtain the Sydnophen intermediate can be completely omitted by the process of this invention.

Hence, in accordance with the first process aspect of this invention, there is provided a method for producing the 3-[1-(hydroxymethyl)-2-phenylethyl)]-N-[(phenylamino)carbonyl]sydnonimines of Formula I, supra, which comprises reacting by nucleophilic addition a compound of the formula:

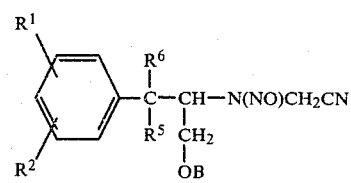

in which B is a hydroxyl protecting group and $R^1$, $R^2$, $R^5$ and $R^6$ are defined above, to an isocyanate of the formula:

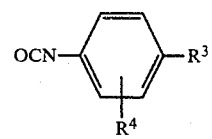

where $R^3$ and $R^4$ are defined above, and subsequently removing the protecting group B.

The hydroxyl protecting groups applicable in the process of this invention are well-known. Exemplary protecting groups are lower alkanoyl of from 1-6 carbon atoms (such as acetyl, propionyl, isopropionyl, etc.), benzoyl, tert-butyl, benzyloxycarbonyl, or silyl ester groups. In selecting a particular hydroxyl protecting group, the criteria for applicability are that the protecting group must be stable during nucleophilic addition to the isocyanate and the protecting group must be removable under reaction conditions which would not otherwise affect the molecule and preferably, where the protecting group is to be retained for use of the compound as a pro-drug, its metabolite should produce no untoward effect. Based upon those standards, the preferred protecting groups are the lower alkanoyl groups. When production of a pro-drug is not desired, it is preferred that the protecting group B be selected to achieve rapid deprotection during and as a result of normal work-up procedures following production of the desired compound. The trimethylsilyl group is ideal for this purpose (although other known silyl protecting groups may be used) because N,O-bis(trimethylsilyl)acetamide is readily available, requires no acid acceptor during reaction with the hydroxyl group, affords neutral or volatile by-products of the silylation reaction and is removed in the normal work-up of the desired product by treatment with an acid to obtain the water-insoluble non-toxic acid addition salt of the Sydnocarb derivative.

Other applicable silyl esters are those tertiary ($R_3$Si— and secondary ($R_2$Si—) silyl moieties in which R is lower alkyl, aryl (preferably the phenyl group) or aralkyl (preferably the phenyl(lower)alkyl group and more preferably benzyl). The tri(lower)alkylsilyl groups being preferred because they are readily hydrolyzed with an alcohol or water to release the free hydroxy substituted product.

Protection of the hydroxymethyl group, when effected with conventional acylating agents such as acetyl chloride, acetic anhydride, and the like, requires the use of at least one equivalent of the acylating agent and one equivalent of an organic base acid receptor such as pyridine. The use of a silyl ester protecting group does not require an acid acceptor. Deprotection is accomplished with a mild base such as sodium or potassium carbonate in protic solvent or with an acid in the case of silyl ester protection.

Thus, as the intermediate compound aspect of this invention there is provided a group of compounds of the formula:

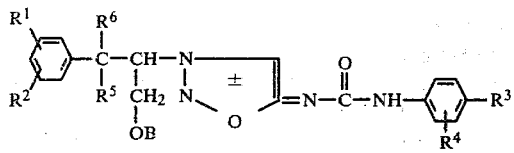

in which $R^1$ to $R^6$ are defined above; and B is a hydroxyl protecting group.

As mentioned previously, certain hydroxy protected sydnocarb derivatives are directly useful as CNS stimulants in that they are equal in activity to the free hydroxy substituted final products. These protected sydnocarb derivatives serve as pro-drugs in that the protecting group is enzymatically removed in vivo to release the free hydroxymethyl sydnocarb derivatives as CNS stimulants. These protected hydroxymethyl sydnocarb derivatives form an additional compound aspect of the invention.

Thus, embraced by formula II are certain pro-drugs such as those in which B is alkanoyl of 1 to 6 carbon atoms, benzoyl, tert-butyl or benzyloxycarbonyl.

In addition, a unique group of pro-drugs reside in hydroxymethyl protected sydnocarb derivatives in which the hydroxy protecting groups are amino substituted acyl moieties such as are represented by the formula:

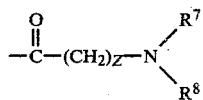

in which
Z is an integer from 1 to 6;
$R^7$ is alkyl of 1 to 6 carbon atoms or aralkyl of 7 to 16 carbon atoms;
$R^8$ is alkyl of 1 to 6 carbon atoms, aralkyl of 7 to 16 carbon atoms, dialkylaminoalkyl of 3 to 18 carbon atoms or diaralkylaminoalkyl of 14 to 32 carbon atoms; or
$R^7$ and $R^8$ are concatenated to form the 4-morpholinyl moiety or a radical of the formulae:

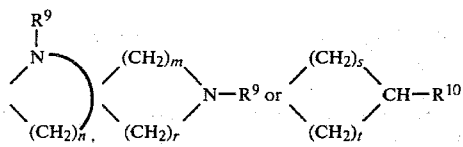

wherein $R^9$ is alkyl of 1 to 6 carbon atoms, aryl of 6 to 10 carbon atoms, hydroxyalkyl of 1 to 6 carbon atoms; aralkyl of 7 to 16 carbon atoms or alkoxyalkyl of 2 to 12 carbon atoms; $R^{10}$ is alkylamino of 1 to 6 carbon atoms or piperidino; n is one of the integers 3, 4 or 5; m is one of the integers 1 or 2; r is one of the integers 2 or 3; s is an integer from 0 to 6; t is an integer from 0 to 6; with the proviso that the sum of s and t is 3 to 6; or a pharmaceutically acceptable salt thereof.

The salts of the aminoacyloxy protected sydnocarb derivatives are water soluble and therefore amenable to administration via an aqueous vehicle. The non-water soluble salt forming and hydrophobic substituted hydroxymethyl sydnocarb pro-drug derivatives are administerable either neat or via suspension or emulsions for lipophilic assimilation and in vivo conversion to the free hydroxy substituted stimulants.

Where desired, the pro-drug compounds embraced by formula II my be produced directly from the final product hydroxymethyl sydnocarb derivatives of my copending application Ser. No. 194,702. Thus, the hydroxymethyl sydnocarb derivatives may be directly acylated with the desired acyl group to obtain the desired pro-drug. With the aminoacyl protecting groups, an indirect preparatory technique may be employed. For example, chloroacetylation of a hydroxymethyl sydnocarb derivative provides an intermediate in which the amino substitutent may be tailored as desired. Thus, the chloroacetylated product is reacted with a desired mono-amine of di-amine (such as those disclosed in U.S. Pat. No. 3,886,276 from which the disclosure of applicable di-amines is incorporated herein by reference) to afford amino acetate esters of the hydroxymethyl sydnocarb derivatives from which pharmaceutically acceptable water-soluble salts are produced. Unlike the Sydnone imine salts of the prior art, the salts formed with the aminoacetate esters of the hydroxymethyl substituted Sydnone imine derivatives of this invention are water-soluble, dissociating sufficiently to dissolve in aqueous medium to provide a homogenous solution. Thus, the salts of the aminoacylated hydroxymethyl sydnocarb derivative may be formulated for administration in aqueous vehicle thereby expanding the routes available for practical dosing to achieve central nervous system stimulation to patients unable to receive treatment orally.

The activity profile of the pro-drug compounds of this invention is similar to that of amphetamine in some aspects while being devoid of other activities of amphetamine. For example, like amphetamine the pro-drug compounds of this invention increase motor activity. However, the pro-drug compounds of this invention are much less toxic than amphetamine, providing a slower onset of activity (which indicates less euphoria and abuse potential).

The pro-drug compounds of this invention were shown to possess central nervous system stimulant activity by subjecting them to the following standard test procedure:

Male mice weighing 17 to 25 gms. are injected orally with drug solubilized or suspended in 1% Tween ® 80. Control animals are injected with 1% Tween ® 80.

Six Columbus Instrument Company activity chambers are employed. Three mice given identical treatment are placed in each chamber for all tests. During each run, control animals (1% Tween ® only) occupy 3 chambers; the other 3 chambers measure activity of drug treated animals. For each dose of a given drug the experiment is run two times in a counterbalanced design so that each specific activity chamber records the activity of control animals during one run, and the activity of drug animals on the other run. Thus, at each dose level 18 mice are used in the drug group and 18 mice in the control group.

Activity counts are recorded every ten minutes for a period of 2 hours. The data are analyzed using Students "t" test comparing the means of the control and drug groups for each 10 minute period. The drug treated group is compared graphically with the control group in regard to duration of action and dose response at peak drug activity.

As central nervous system stimulants with unique activity profiles, the pro-drug compounds of this invention are useful in the treatment of anergic disorders (such as sleepiness and fatigue) including related types of depression and narcolepsy. Based upon the potency of the compounds of this invention in use in mice, the dose contemplated for use in the 70 kilogram human would vary from about 35–700 milligrams administered orally once or twice per day under the guidance of a physician. Of course, the dosage regimen as well as the route of administration, oral or parenteral, will vary with the condition of the patient relative to age, severity of depression, etc.

The following examples illustrate, without limitation, the novel process for producing the 3-[(hydroxymethyl)-2-phenylethyl]sydnocarb derivatives of my copending application, Ser. No. 194,702, the intermediates formed in that process, the hydroxymethyl substituted pro-drug compounds and the direct production of those pro-drug compounds from the products disclosed in said copending application. Activity counts represent the difference from control. l-Sydnocarb presents a difference from control of 939 counts at 10 mg/kg.

EXAMPLE 1

1-[[1-[(Acetyloxy)methyl]-2-phenylethyl]nitrosoamino]acetonitrile

Dissolve 1-[[1-(hydroxymethyl)-2-phenylethyl]nitrosoamino]acetonitrile (2.19 g.) in methylene chloride (25 ml.), add pyridine (2.37 g.) followed by acetic anhydride (3.06 g.) and let the reaction stand at room temperature overnight. Wash the reaction with 2 N aqueous-HCl, saturated sodium carbonate solution, brine and dry. Evaporate the extract in vacuo and pump the residue. Dissolve the resulting oil in diethyl ether-methylene chloride, treat with decolorizing carbon, filter and evaporate in vacuo. Crystallize the resulting oil from diethyl ether, filter and dry to obtain 2.25 g. of the title product; m.p. 56°–59° C.; $[\alpha]_D^{24.5} = -58.81°$ (0.935% in methanol).

Analysis for: $C_{13}H_{15}N_3O_3$; Calculated: C, 59.76; H, 5.79; N, 16.08%; Found: C, 59.50; H, 5.68; N, 15.95%.

EXAMPLE 2

1-3-[1-[(Acetyloxy)methyl]-2-phenylethyl]-N-[[(4-chlorophenyl)amino]carbonyl]sydnone imine Stir 1-[[1-[(acetyloxy)methyl]-2-phenylethyl]nitrosoamio]acetonitrile (4.09 g.) in toluene (100 ml), add triethylamine (1.75 g.) followed by 4-chlorophenylisocyanate (2.65 g). Heat the reaction on the steam-bath for 2 hours, let cool and stand at room temperature overnight. Filter the resulting solid to obtain 3.83 g. of the crude title product; m.p. 134°–137° C. Dissolve 2.83 g. of the product in methylene chloride, treat with decolorizing carbon, filter, then boil off the solvent and replace with isopropanol by boiling. Let cool, scratch and let stand to complete crystallization. Filter and dry to get 1.94 g. of the pure title product; m.p. 135°–137° C.; $[\alpha]_D^{25} = -200.63°$ (1.515% in methanol).

Analysis for: $C_{20}H_{19}ClN_4O_4$; Calculated: C, 57.90; H, 4.62; N, 13.51; Cl, 8.55%; Found: C, 57.76; H, 4.58; N, 13.60; Cl, 8.21%; Activity Counts: 1576 p<0.01 at 10 mg/kg; 709 p<0.01 at 1 mg/kg.

EXAMPLE 3

1-N-[[(4-Chlorophenyl)amino]carbonyl]-3-[1-(hydroxymethyl)-2-phenylethyl]sydnone imine Stir 1-3-[1-[(acetyloxy)methyl]-2-phenylethyl]-N-[[(4-chlorophenyl)amino]carbonyl]sydnone imine (1.00 g.) and methanol (100 ml), then add solid potassium carbonate (1.0 g.). Stir for 3 hours, filter, then evaporate the solvent in vacuo. Digest the residue with water and methylene chloride. Wash, dry and evaporate the methylene chloride extract in vacuo. Cover the residue with diethyl ether, then add a little isopropanol to solubilize. Let stand to crystallize, then filter to obtain 0.69 g. of the title product, m.p. 156.5°–158.5° C. Combine the products from several experiments (2.34 g.) and dissolve in methylene chloride containing methanol. Treat the solution with decolorizing carbon, filter and evaporate the solvents in vacuo. Cover the gum with diethyl ether, add enough isopropanol to solubilize, then let stand to crystallize. Filter and dry to obtain 1.92 g. of the pure title product; m.p. 155°–157° C.; $[\alpha]_D^{25.5°} = -125.7°$ (1.005% in methanol).

Analysis for: $C_{18}H_{17}ClN_4O_3$; Calculated: C, 57.99; H, 4.60; N, 15.02; Cl, 9.51%; Found: C, 57.85; H, 4.60; N, 15.33; Cl, 9.43%.

EXAMPLE 4

1-N-[[(4-Chlorophenyl)amino]carbonyl]-3-[1-(hydroxymethyl)-2-phenylethyl]sydnone imine Stir 1-[[1-(hydroxymethyl)-2-phenylethyl]nitrosoamino]acetonitrile (2.19 g.) and toluene (20 ml.), cool, add triethylamine (2.02 g.), then acetyl chloride (0.79 g.). Stir for 1 hour at room temperature, then add 4-chlorophenylisocyanate (1.53 g.) and heat on the steam-bath for 3 hours. Let stand at room temperature. Dilute the reaction with ethyl acetate, wash with 2 N aqueous HCl, water, brine, then dry and evaporate in vacuo. Dissolve the resulting oil in chloroform, pass through a short column of silica gel and evaporate the chloroform to obtain a yellow oil. Dissolve the oil in methanol (50 ml.), add solid potassium carbonate (2.0 g.) and stir at room temperature for 2 hours. Let stand, then add brine and extract with methylene chloride. Dry, then evaporate the solvent in vacuo and pump dry. Dissolve the oil in methylene chloride, treat with decolorizing carbon, filter and evaporate the solvent in vacuo. Cover the oil with diethyl ether, add a little isopropanol to solubilize. Let stand, then filter to obtain 0.41 g. of the title product; m.p. 151°–154° C. The product is identical to that of the previous example.

EXAMPLE 5

1-N-[[(4-Chlorophenyl)amino]carbonyl]-3-[1-(hydroxymethyl)-2-phenylethyl]sydnone imine, hydrochloride Stir 1-[[1-(hydroxymethyl)-2-phenylethyl]nitrosoamino]acetonitrile (2.19 g.) with toluene (100 ml.), add N, O-bis-(trimethylsilyl)-acetamide (6.09 g.), then continue stirring for 2 hours, or at least for 1 hour beyond the point at which the solution becomes clear. Evaporate the solvent in vacuo and pump to remove excess silylation reagent and byproducts. Redissolve the oil in toluene (100 ml.), add 4-chlorophenyl-isocyanate (1.68 g.) followed by triethylamine (1.10 g.). Warm the mixture gently on the steam-bath for 2½ hours. Let cool and stand at room temperature overnight. Filter and evaporate the filtrate in vacuo. Dissolve the oil in chloroform and add just enough ethyl acetate to solubilize. Shake the extract well with excess 2 N aqueous HCl solution. Filter the resulting solid to obtain 2.070 g. of crude title product; m.p. 156°–157° C. (dec). Dissolve the solid in methylene-chloride-methanol, treat with decolorizing carbon, filter and evaporate the solvents in vacuo to obtain a glass. Crystallize the product from acetone and filter to obtain 1.531 g; m.p. 150.0°–151.5° C. (dec); $[\alpha]_D^{26.5} = -154.87°$ (0.99% in methanol).

EXAMPLE 6 dl-3-[1-[(Chloroacetyloxy)methyl]-2-phenylethyl]-N-[(phenylamino)carbonyl]sydnone imine Stir dl-3-[1-(hydroxymethyl)-2-phenylethyl]-N-[(phenylamino)carbonyl]sydnone imine (6.18 g.) with tetrahydrofuran (100 ml.) under nitrogen, then add 4-dimethylaminopyridine (2.23 g.) followed by chloroacetylchloride (2.06 g.) dropwise and with continued stirring. Stir for 3 hours. Filter and evaporate the solvent in vacuo and pump to an oil. Treat the oil in methylene chloride with decolorizing carbon, filter and evaporate the solvent in vacuo. Warm the resulting gum with isopropanol to dissolve, then let cool slowly to crystallize. Filter to obtain 6.60 g. of the title product; m.p. 136°–140° C. Dissolve 2.81 g. of the product in methylene chloride treat with decolorizing carbon, filter, then replace the solvent with isopropanol by boiling on the steam bath. Let cool, add several drops of ethyl acetate to remove cloudiness, seed and let stand to crystallize. Filter to obtain 2.36 g. of pure title product; m.p. 141.0°–143.5° C.

Analysis for: $C_{20}H_{19}ClN_4O_4$; Calculated: C, 57.90; H, 4.62; N, 13.51%; Found: C, 57.56; H, 4.61; N, 13.47%.

EXAMPLE 7 dl-3-[1-[[(4-Methyl-1-piperazinyl)acetyloxy]methyl]-2-phenylethyl]N-[(phenylamino)carbonyl]sydnone imine, trihydrochloride Stir dl-3-[1-[(chloroacetyloxy)methyl]-2-phenylethyl]N-[(phenylamino)carbonyl]sydnone imine (4.15 g.) in methylene chloride (50 ml), cool with an ice-bath, then add triethylamine (1.02 g.) followed by N-methylpiperazine (1.01 g.) using methylene chloride to rinse in the reagents. Stir under nitrogen for 3 hours at room temperature. Let stand overnight. Wash the reaction with water, brine and then evaporate the solvent in vacuo and pump to a glass. Treat the glass in methylene chloride with decolorizing carbon, filter and treat the filtrate with 5 N isopropanolic-HCl (5 ml). Evaporate the solvents in vacuo and pump to a glass. Cover the glass with acetone and triturate, then decant the solvent. Repeat the trituration and decantation with acetone twice more, then filter and dry to get 3.75 g. of the crude title product; m.p. 147°–152° C. (dec). Dissolve 3.55 g. of the product in methylene-chloride containing some methanol, boil and replace the solvents with acetonitrile by boiling on the steam-bath. Let cool to form a gum. Add a little methylene chloride dropwise and scratch until crystalline. Filter and dry to obtain 1.98 g. of the title product as a hemihydrate; m.p. 158°–160° C. (dec).

Analysis for: $C_{25}H_{30}N_6O_4 \cdot 3HCl \cdot \frac{1}{2}H_2O$; Calculated: C, 50.30; H, 5.74; N, 14.08; Cl, 17.82%; Found: C, 50.37; H, 5.50; N, 14.35; Cl, 17.66%; Activity Counts: 407 $p < 0.05$ at 10 mg/kg.

EXAMPLE 8 dl-3-[1-[[(4-Morpholinyl)acetyloxy]methyl]-2-phenylethyl]-N-[(phenylamino)carbonyl]sydnone imine, dihydrochloride Dissolve dl-3-[1-[(chloroacetyloxy)methyl]-2-phenylethyl]-N-[(phenylamino)carbonyl]sydnone imine (4.15 g.) in tetrahydrofuran (100 ml.), then add triethylamine (1.11 g.) followed by morpholine (0.95 g). Swirl and let the reaction stand at room temperature for two days. Evaporate the solvent in vacuo, dissolve the residue in methylene chloride and treat the solution with 5 N isopropanolic-HCl (5 ml). Evaporate the solvents in vacuo and cover the resulting glass with water and triturate well. Treat with decolorizing carbon, filter, then treat the aqueous layer with solid potassium carbonate to a pH of about 10 (3.5 g). Quickly extract the mixture with methylene chloride, then wash, dry and evaporate the methylene chloride in vacuo. Pump the residue dry to an oil, then treat the oil in methylene chloride with decolorizing carbon. Filter, then treat the filtrate with 5 N isopropanolic-HCl (5 ml). Evaporate the solvents in vacuo. Dissolve the resulting glass in acetonitrile and let stand to crystallize. Filter and dry to obtain 4.20 g. of the title product; m.p. 138°–140° C. (dec). Dissolve the solid in methylene chloride containing methanol, treat with decolorizing carbon, filter and evaporate the solvents in vacuo. Dissolve the resulting gum in acetonitrile, seed and let stand to crystallize. Filter and dry to obtain 3.94 g. of the title product as an acetonitrile solvate; m.p. 144°–146° C. (dec). The solid will be a crystalline solvate of acetonitrile. Dissolve the solid in methylene chloride containing methanol, treat with decolorizing carbon, filter and evaporate the solvents in vacuo. Cover the gum with isopropanol, add a little methanol to solubilize, then evaporate the solvents in vacuo and in the cold. Digest the resulting solid with isopropanol, filter and dry to obtain 2.16 g. of the title product as a hemihydrate, hemi-isopropanol solvate; m.p. 142° C.

Analysis for: $C_{24}H_{27}N_5O_5 \cdot 2HCl \cdot \frac{1}{2}C_3H_8O \cdot \frac{1}{2}H_2O$; Calculated: C, 53.03; H, 5.93; N, 12.13; Cl, 12.28%; Found: C, 53.09; H, 5.83; N, 12.47; Cl, 12.18%; Activity Counts: 584 $p < 0.01$ at 10 mg/kg.

EXAMPLE 9 dl-3-[1-[[(Diethylamino)acetyloxy]methyl]-2-phenylethyl]-N-[(phenylamino)carbonyl]sydnone imine, dihydrochloride Dissolve dl-3-[1-[(chloroacetyloxy)methyl]-2-phenylethyl]-N-[(phenylamino)carbonyl]sydnone imine (3.86 g.) in tetrahydrofuran (75 ml.), add triethylamine (1.03 g.), then diethylamine (0.75 g). Stir the reaction at room temperature for 3 hours, then let stand for 2 days. Add another 1 ml. of diethylamine, stir, then evaporate the reaction in vacuo. Dissolve the residue in methylene chloride, treat the solution with 5 N isopropanolic-HCl (5 ml), then evaporate the solvents in vacuo and pump. Cover the residue with water, triturate, treat with decolorizing carbon and filter. Treat the aqueous filtrate with solid potassium carbonate (3.5 g). Quickly extract with methylene chloride, then wash, dry and evaporate the extract in vacuo. Pump to a dry oil. Dissolve the oil in methylene chloride and treat with 5 N isopropanolic-HCl (5 ml). Evaporate the solvents in vacuo, then cover the resulting glass with acetone and cool with scratching until crystalline. Filter and dry to obtain 2.60 g. of the crude title product; m.p. 153°–156° C. (dec). Dissolve the solid in methylene chloride containing a little methanol, treat with decolorizing carbon, then filter and evaporate the solvents in vacuo. Dissolve the resulting oil in acetonitrile, filter and scratch to initiate crystallization. Let stand, then filter to obtain 2.73 g. of the pure title product; m.p. 156°–157° C. (dec).

Analysis for: $C_{24}H_{29}N_5O_4\cdot 2HCl$; Calculated: C, 54.96; H, 5.96; N, 13.36; Cl, 13.52%; Found: C, 54.87; H, 5.78; N, 13.40; Cl, 13.19%; Activity Counts: 519 p<0.01 at 10 mg/kg.

EXAMPLE 10

1-N-[[(4-Chlorophenyl)amino]carbonyl]-3-[1-[[(4-morpholinyl)acetyloxy]methyl]-2-phenylethyl]sydnone imine, dihydrochloride Dissolve 1-[[1-(hydroxymethyl)-2-phenylethyl]nitrosoamino]acetonitrile (6.58 g.) in methylene chloride (75 ml), add pyridine (4.75 g.) followed by chloroacetic anhydride (10.26 g). Swirl until homogeneous, let stand, then wash the methylene chloride solution with saturated sodium carbonate solution, with brine and dry the extract. Evaporate the solvent in vacuo and pump dry to obtain the chloroacetate ester as an oil. Dissolve the oil (4.218 g.) in tetrahydrofuran (100 ml.), add triethylamine (1.60 g.) in tetrahydrofuran (5 ml.) followed by morpholine (1.40 g.) in tetrahydrofuran (5 ml). Stir for 3 hours, then let stand overnight at room temperature. Evaporate the solvent in vacuo, dissolve the resulting oil in methylene chloride and wash the extract with water, brine and dry. Evaporate the extract in vacuo, then treat the resulting dry oil in methylene chloride with decolorizing carbon. Filter, evaporate the solvent in vacuo, then pump dry to obtain the intermediate (4-morpholinyl)acetate ester as an oil. Dissolve the oil in toluene (100 ml) and triethylamine (3.03 g) followed by 4-chlorophenylisocyanate (4.61 g). Heat the reaction gently on the steam-bath for 2 hours, then let cool and stand at room temperature overnight. Filter and evaporate the toluene in vacuo. Dissolve the residue in methylene chloride, wash with water, brine and dry. Evaporate the solvent in vacuo and pump dry. Treat the resulting gum in methylene chloride with 5 N isopropanolic-HCl (10 ml) and evaporate the solvents in vacuo and pump dry. Cover the residue with water and triturate well. Treat with decolorizing carbon, filter, then add methylene chloride to the filtrate. Treat with solid anhydrous potassium carbonate (8.3 g.) and shake well. Extract the aqueous with methylene chloride, then wash dry and evaporate the combined extracts in vacuo. Pump the residue to obtain the free base of the product as a glass. Treat the glass in methylene chloride with decolorizing carbon, filter and evaporate the solvent in vacuo. Treat the resulting glass in methylene chloride with 5 N isopropanolic-HCl (10 ml). Evaporate the solvents in vacuo. Dissolve the residue in acetonitrile and let stand to crystallize. Filter to obtain 3.219 g. of the crude title product; m.p. 151°–155° C. (dec). Dissolve the solid in methylene chloride-methanol, treat with decolorizing carbon, filter, then evaporate the solvents in vacuo and pump the residue dry. Cover with acetone, triturate, then filter to obtain the title product as a partial acetone solvate (2.883 g.); m.p. 145°–148° (dec); $[\alpha]_D^{25.5°} = -68.54°$ (1.20% in methanol).

Analysis for: $C_{24}H_{26}ClN_5O_5\cdot 2HCl\cdot\frac{1}{4}C_3H_6O$; Calculated: C, 50.60; H, 5.06; N, 11.92; Cl, 18.11%; Found: C, 50.27; H, 5.17; N, 12.19; Cl, 17.90%; Activity Counts: 1281 p<0.01 at 1 mg/kg.

What is claimed is:

1. A hydroxyl protected 3-[1-(hydroxymethyl)-2-phenylethyl)]-N-[(phenylamino)carbonyl]sydnone imine derivative of the formula:

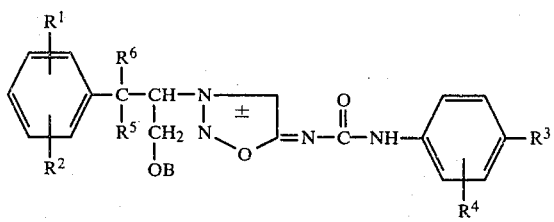

in which
 $R^1$ and $R^2$ are, independently, hydrogen, alkyl of 1 to 6 carbon atoms, alkoxy of 1 to 6 carbon atoms, halo, perfluoroalkyl of 1 to 3 carbon atoms, nitro, alkanoyl of 2 to 4 carbon atoms, or alkoxycarbonyl of 2 to 4 carbon atoms;
 $R^3$ is hydrogen, halo, nitro or alkanoyl of 2 to 4 carbon atoms;
 $R^4$ is hydrogen, halo, nitro or perfluoroalkyl of 1 to 3 carbon atoms;
 $R^5$ and $R^6$ are, independently, hydrogen, methyl or ethyl and
 B is a hydroxy protecting group.

2. A hydroxyl protecting compound of claim 1 in which B is alkanoyl of 1 to 6 carbon atoms, benzoyl, tert-butyl, benzyloxycarbonyl or silyl ester group.

3. The compound of claim 2 which is 3-[1-(acetyloxymethyl)-2-phenylethyl]-N-[[(4-chlorophenyl)amino]carbonyl]sydnonimine or a non-toxic acid addition salt thereof.

4. The compound of claim 2 which is 3-[1-(trimethylsilyloxymethyl)-2-phenylethyl]-N-[[(4-chlorophenyl)amino]carbonyl]sydnonimine.

5. A compound of claim 1 which is 3-[1-(aminoacyloxymethyl)-2-phenylethyl]-N-[(phenylamino)carbonyl]sydnone imine derivative of the formula:

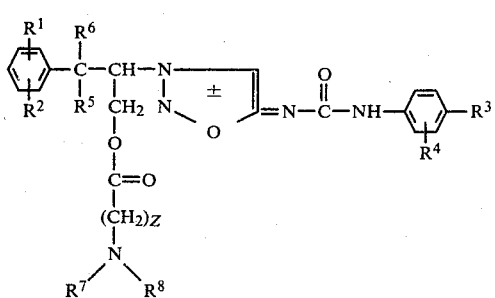

in which
 $R^1$ and $R^2$ are, independently, hydrogen, alkyl of 1 to 6 carbon atoms, alkoxy of 1 to 6 carbon atoms, halo, perfluoroalkyl of 1 to 3 carbon atoms, nitro, alkanoyl of 2 to 4 carbon atoms or alkoxycarbonyl of 2 to 4 carbon atoms;
 $R^3$ is hydrogen, halo, nitro or alkanoyl of 2 to 4 carbon atoms;

$R^4$ is hydrogen, halo, nitro or perfluoroalkyl of 1 to 3 carbon atoms;

$R^5$ and $R^6$ are, independently, hydrogen or methyl;

Z is an integer from 1 to 6;

$R^7$ is alkyl of 1 to 6 carbon atoms or aralkyl of 7 to 16 carbon atoms;

$R^8$ is alkyl of 1 to 6 carbon atoms, aralkyl of 7 to 16 carbon atoms, dialkylaminoalkyl of 3 to 18 carbon atoms or diaralkylaminoalkyl of 14 to 32 carbon atoms;

or $R^7$ and $R^8$ are concatenated to form the 4-morpholinyl moiety or a radical of the formulae:

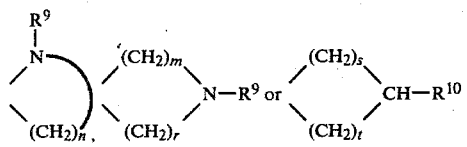

wherein $R^9$ is alkyl of 1 to 6 carbon atoms, aryl of 6 to 10 carbon atoms, hydroxyalkyl of 1 to 6 carbon atoms; aralkyl of 7 to 16 carbon atoms or alkoxyalkyl of 2 to 12 carbon atoms; $R^{10}$ is alkylamino of 1 to 6 carbon atoms or piperidino; n is one of the integers 3, 4 or 5; m is one of the integers 1 or 2; r is one of the integers 2 or 3; s is an integer from 0 to 6; t is an integer from 0 to 6; with the proviso that the sum of s and t is 3 to 6.

6. The compound of claim 5 which is d,l-3-[1-[[(4-methyl-1-piperazinyl)acetyloxy]methyl]-2-phenylethyl]-N-[(phenylamino)carbonyl]-sydnone imine or a pharmaceutically acceptable salt thereof.

7. The compound of claim 5 which is d,l-3-[1-[[(4-morpholinyl)acetyloxy]methyl]-2-phenylethyl]-N-[(phenylamino)carbonyl]sydnone imine or a pharmaceutically acceptable salt thereof.

8. The compound of claim 5 which is d,l-3-[1-[[(diethylamino)acetyloxy]methyl]-2-phenylethyl]-N-[(phenylamino)carbonyl]sydnone imine or a pharmaceutically acceptable salt thereof.

9. The compound of claim 5 which is l-N-[[(4-chlorophenyl)amino]carbonyl]-3-[1-[[(4-morpholinyl)acetyloxy]methyl]-2-phenylethyl]sydnone imine or a pharmaceutically acceptable salt thereof.

* * * * *